(12) United States Patent
Alexander

(10) Patent No.: US 9,764,170 B2
(45) Date of Patent: Sep. 19, 2017

(54) HYPOXIA RECOVERY SYSTEM FOR MASK OFF HYPOXIA TRAINING

(71) Applicant: Walter E. Alexander, Pensacola, FL (US)

(72) Inventor: Walter E. Alexander, Pensacola, FL (US)

(73) Assignee: The United States of America as represented by Secretary of the navy, Washington, DC (US)

(*) Notice: Subject to any disclaimer, the term of this patent is extended or adjusted under 35 U.S.C. 154(b) by 190 days.

(21) Appl. No.: 14/575,242

(22) Filed: Dec. 18, 2014

(65) Prior Publication Data

US 2016/0175623 A1    Jun. 23, 2016

(51) Int. Cl.
| | | |
|---|---|---|
| G09B 9/08 | (2006.01) | |
| A62B 7/14 | (2006.01) | |
| G09B 23/28 | (2006.01) | |
| G09B 9/00 | (2006.01) | |
| G09B 9/16 | (2006.01) | |
| A61G 10/02 | (2006.01) | |
| A61M 16/00 | (2006.01) | |
| A61M 16/10 | (2006.01) | |

(52) U.S. Cl.
CPC .............. *A62B 7/14* (2013.01); *A61G 10/023* (2013.01); *G09B 9/00* (2013.01); *G09B 9/165* (2013.01); *G09B 23/28* (2013.01); *A61M 16/0045* (2013.01); *A61M 16/107* (2014.02); *A61M 2205/33* (2013.01); *A61M 2205/42* (2013.01); *A61M 2205/82* (2013.01)

(58) Field of Classification Search
USPC ......... 434/30, 37, 59, 247, 262; 128/202.12, 128/204.18, 205.11, 205.12
See application file for complete search history.

(56) References Cited

U.S. PATENT DOCUMENTS

| | | | | | |
|---|---|---|---|---|---|
| 5,101,819 | A | * | 4/1992 | Lane .................... | A61G 10/023 128/204.18 |
| 5,799,652 | A | * | 9/1998 | Kotliar .................. | A61G 10/00 128/200.24 |
| 5,924,419 | A | * | 7/1999 | Kotliar .................. | A23L 3/3418 128/200.24 |
| 6,009,870 | A | * | 1/2000 | Tkatchouk ............. | B01D 53/22 128/202.12 |
| 6,561,185 | B1 | * | 5/2003 | Kroll ..................... | A61M 16/10 128/202.12 |
| 6,565,624 | B2 | * | 5/2003 | Kutt ....................... | A61G 10/02 128/202.12 |

(Continued)

OTHER PUBLICATIONS

The NAVEDTRA 14327, Aviation Structural Mechanic E, Navy course publication.

*Primary Examiner* — Kurt Fernstrom
(74) *Attorney, Agent, or Firm* — Albert M. Churilla; Ning Yang; Diane Tso

(57) ABSTRACT

A hypoxia recovery system capable of supplying breathing air with approximately 20% oxygen to a subject inside a mask off hypoxia training room without the use of a real world MD-1 aviator oxygen regulator, yet have the experience and realism of a real world MD-1 aviator oxygen regulator. The invention also teaches a method of hypoxia flight training, using said hypoxia recovery system.

10 Claims, 5 Drawing Sheets

(56) References Cited

U.S. PATENT DOCUMENTS

| | | | | |
|---|---|---|---|---|
| 7,011,092 B2* | 3/2006 | McCombs | ........ | A61M 16/0045 128/205.11 |
| 8,375,938 B2* | 2/2013 | Gaumond | ............ | A61G 10/026 128/202.12 |
| 8,535,064 B2* | 9/2013 | Linton | .................. | A61G 10/026 128/202.12 |
| 2003/0070678 A1* | 4/2003 | Wartman | .......... | A61M 16/0045 128/203.14 |
| 2005/0202374 A1* | 9/2005 | Stepanek | ............. | A61G 10/026 434/37 |
| 2005/0247311 A1* | 11/2005 | Vacchiano | ........ | A61M 16/0045 128/203.12 |
| 2014/0322675 A1* | 10/2014 | Bassovitch | .............. | G09B 9/10 434/59 |

* cited by examiner

| SWITCH POSITIONING | | |
|---|---|---|
| OFF/ON | OFF | ON |
| NORMAL | ⊘ | 5 LPM |
| EMERGENCY | ⊘ | 15LPM |
| TEST MASK | ⊘ | 30 LPM |

FIGURE 5

HYPOXIA RECOVERY SYSTEM FOR MASK OFF HYPOXIA TRAINING

CROSS-REFERENCE TO RELATED APPLICATIONS

This application claims priority to U.S. Provisional Application 61/917,444 filed Dec. 18, 2013.

FIELD OF INVENTION

This invention is related to high altitude, in-flight hypoxia recognition training. In particular, this invention is related to a positively pressured breathing system used in hypoxia recovery by aircrew assigned to pressurized cabin aircraft during mask-off hypoxia recognition training. This invention is also directed to a method of hypoxia recovery from the severe physiological symptoms, of exposure to low oxygen concentrations, experienced in a normobaric, high altitude simulation enclosure.

BACKGROUND

Hypoxia is a condition in which the body or a region of the body is deprived of an adequate oxygen supply needed to sustain cognitive brain function and prevent tissue and organ damage. Generalized hypoxia can occur in healthy people during flight, due to a decrease in the partial pressure of oxygen in inspired air as altitude increases beyond the limits of human physiological compatibility. Hypoxia, or altitude sickness, is the number two leading cause of aircraft mishaps, and can lead to potentially fatal complications, such as high altitude pulmonary edema (HAPE), high altitude cerebral edema (HACE), and ultimately hypoxic loss of consciousness (HLOC).

For years, cabin pressurization and onboard oxygen systems have allowed for normal in-flight high altitude aviation activities by aircrew, within the aircraft. However, flight safety with regard to hypoxia, is still limited by the failure of the onboard flight oxygen equipment, and aircraft structural failures. For example, most commercial aircraft maintain a cabin pressure of 8,000 ft, and all unpressurized aircraft operate below a 10,000 ft. ceiling, which are ideal for preventing hypoxia from occurring. Combat aircraft has a higher altitude operational ceiling, and their onboard oxygen systems are used invariably, until a safe breathable altitude is reached. The threat of hypoxia is ever present with an accidental loss of cabin pressurization, or when flying unpressurized aircraft beyond the maximum altitude in which the ambient air is not suitable for unaided breathing. On Aug. 14, 2003, 6 crew and 115 passengers perished in the crash of Greece Helios Airways Boeing 737-300 due to loss of cabin pressurization. This hypoxia related accident along with many others, is why hypoxia recognition and recovery, remains a major interest in both military and civil aviation training.

Aviation related hypoxia is known as hypobaric hypoxia, which is caused by breathing air at altitudes above 10,000 feet. When altitude increases, the partial pressure of oxygen, in the inspired air, is progressively reduced. This is compared to a normal barometric pressure of 160 mm Hg and a 20.9% oxygen concentration while breathing air at sea level. The typical causes of accidental hypoxia in flight include: ascent to altitude without a supplemental oxygen supply, failure of personal or aircraft oxygen breathing equipment, or decompression (loss) of aircraft cabin pressure.

The signs and symptoms of hypoxia become apparent as the degree of hypoxia increases. This can include: shortness of breath, air hunger, excessive yawning, tiredness, fatigue, euphoria, physical impairment, mental impairment, altered phisio-sensory mechanisms, or any combination of these, which can ultimately lead to a complete loss of consciousness (HLOC). An individual's hypoxia symptoms are affected by many different physiological factors, which differ for from person or person. Among them, the factors include varied flight dynamics, such as, altitude, rate of ascent, duration at an altitude, ambient temperature, the physical activity of an individual, the individual's own unique susceptibility, his/her health and physical fitness. There is no noticeable symptom of discomfort or pain associated with the onset of hypoxia. It is therefore vital, that each flight crew member is trained to recognize his/her "individual" hypoxia symptoms, as the onset symptoms of hypoxia can be insidious subtle and can begin without any conscience warning.

The key to dealing with the altitude sickness is taking advantage of the body's ability to gradually acclimatize slowly through a transition of progressively higher altitudes. The body adjusts to altitude by increasing respiratory volume, increasing pulmonary artery pressure, cardiac output, the number of red blood cells, oxygen carrying capability of red blood cells, and by even changing body tissues to promote normal function at lower oxygen levels.

Low pressure chambers are typically used in the United States for aviation hypoxia training. Nearly 10,000 students receive hypobaric training in the U.S. Navy annually. The training consists of exposure to hypobaric environments at or above altitudes of 20,000 feet. The incidence of decompression illness resulting from hypobaric chamber training has been reported by a number of military training organizations. A review of 10 of these reports shows a range of incidence in various populations from 0.3 to 2.9 cases per 1000 exposures, with a mean incidence of 1 case per 1000 exposures (or 0.1%). The Navy has average 4 cases of Decompression Sickness (DCS) annually in its hypobaric chambers with an associated cost of several thousand dollars per treatment, and the possibility of long term medical complications for the patient. These chambers are expensive to construct and operate, and only a limited number of these chambers are available. Despite their relatively large size, the chambers are still relatively small to allow incorporation of mission simulators into the hypoxic environment. Some investigators believe that if hypoxia training and flight training could be combined, the realism of the training scenario would be greatly improved, and the overall training benefit would be significantly increased for aircrew.

The U.S. Navy has had outstanding success in using mixed gas (normobaric hypoxia) mask on training devices for hypoxia recognition/recovery training for tactical jet aviators, while using the Reduced Oxygen Breathing Device (herein "ROBD" as described in U.S. Pat. No. 6,871,645 and "ROBD2" as described in US Pub. 20050247311). ROBD/ROBD2 training devices uses an aviator's mask to deliver a reduced oxygen content mixed gas, to the individual aviator. This gas mix is adjusted to increase or decrease the oxygen concentration, for any altitude for which the ROBD/ROBD2 is programmed to attain. Although ROBD units can reduce the danger of decompression illness, caused by hypobaric chambers, they are less suitable for training of multi-crew pressurized aircraft aviator aircrew. The hypoxia training for pressurized aircraft crew training would most likely involve a "mask off" hypoxia training scenario. It is of paramount importance that aircrew communication and coordination is practiced while training multi-crew pressurized aircraft students on hypoxia recognition and recovery. Therefore, there is a need for a realistic, mask-off, sea-level (normobaric) hypoxia training system. This type of hypoxia training environment alleviates any aircrew student from ever having decompression sickness occur, as there is no barometric pressure change within a hypoxia enclosure/room, as opposed to the barometric pressure changes experienced while aircrew train in a "hypobaric" altitude chamber.

Several companies have developed normobaric (no barometric pressure change) reduced oxygen concentration training environment, in a relatively large sealed space. These reduced oxygen rooms are capable of maintaining reduced oxygen environments, which emulate altitudes in excess of 30K feet. For example, Colorado Altitude Training LLC (Louisville, Colo.) has built several product lines for sport, military and aviation purposes, including a hypoxic sleeping system, a hypoxic exercising system, a free-standing enclosure system, an environmental chamber conversion system, a hyperoxic (oxygen-rich) system, and an aviation systems simulating up to 30,000 feet. An example of a CAT system and a method for passive hypoxic training is described in U.S. Pat. No. 6,827,760 to Kutt. The 760's system comprises an oxygen concentrator, sensors for oxygen, temperature, $CO_2$ and ambient pressure, and a $CO_2$ scrubber, which eliminates $CO_2$ to keep the air fresh and clean within the chamber. Also included in the 760's system is a ventilation fan, a vent, a gate, and a blower, which brings in fresh air when oxygen levels fall below desired levels, or when carbon dioxide levels rise above desired levels, and if either oxygen or $CO_2$ are outside of their safe range. A controller is used to regulate the oxygen concentrator, the $CO_2$ scrubber, and the ventilation fan so the percentage of oxygen in the room can be altered by removing carbon dioxide, and bringing in fresh air. The controller also monitors oxygen and carbon dioxide levels.

Colorado Altitude Training (CAT) LLC., aviation hypoxic training chamber is based on a double tent design, which may be adapted from any sufficiently sealed space. A pressure transducer is used to determine the natural elevation. The controllers are self-calibrating, can provide up to 42 days of data logging, and have remote display capability. In current sports and athletic hypoxia training, using the CAT room, hypoxia recovery is accomplished using a medical grade oxygen mask that supplies 100% $O_2$. Although, the CAT hypoxia recovery system employs the emergency oxygen masks found on commercial airplanes, and in other commercially available hypobaric attitude chambers, because the user is wearing an air mask throughout the training, it fails simulate realistic conditions of hypoxia event for the aircrew of a pressurized aircraft and thus not suited for mask-off hypoxia recovery training. Furthermore, the operations of these chambers are both expensive and labor intensive. The recovery system often requires large volumes of onsite oxygen storage, as 100% oxygen is supplied to multiple aircrew trainees and instructor, during the hypoxia recovery training. The oxygen storage requirement is particularly unfeasible due to strict restriction under fire code regulations regarding storing and supplying large quantities of 100% oxygen. A typical mask-off hypoxia training chamber needs an OSHA approved gas storage room to be build. Bank of multiple "T-bottles" hospital grade oxygen need to be connected to the chamber via manifold and plumbing. The system is also expensive to operate. Four bottles of oxygen only last about 10-15 lab sessions, and need to be automatically switches to the other oxygen source when line pressure reaches a threshold.

The current invention aims to alleviate many of the problems associated with the current hypoxia recovery systems. A mask-off hypoxia system for a pressurized aircraft of this invention, would provide realistic simulations of different hypoxia events, and allow multi-crew hypoxia recovery drills, which may include drills on hypoxia recognition, crew-communication and hypoxia recovery.

DESCRIPTION OF THE FIGURES

FIG. 5 is a table showing the control setting on a mock MD-1 control panel and their corresponding flow rates to the student's breathing mask

DESCRIPTION OF THE INVENTION

This invention describes a hypoxia recovery system that supplies sea-level air to the aircrew trainees and observers/instructor inside a normobaric aviation training chamber, during mask off hypoxia recognition and recovery training. The inventive device eliminates the expense and difficulties associated with oxygen storage and maintenance of existing aviation normobaric training chamber. This invention adopts an emulated aircraft style oxygen recovery system, which comprises a mock MD-1 panel mount aircraft regulator, an air delivery system, and a control system. The mock aircraft Md-1 aircraft oxygen regulator provides the users with positive pressured ambient air at three selectable flow rates, via aviator's breathing mask, without the need for a 100% O2 and thus eliminates the need of associated hardware and an oxygen source. This invention greatly improves training realism, can be easily maintained at reduced cost compare to traditional 100% oxygen aircraft hypoxia recovery system.

Figure 1:
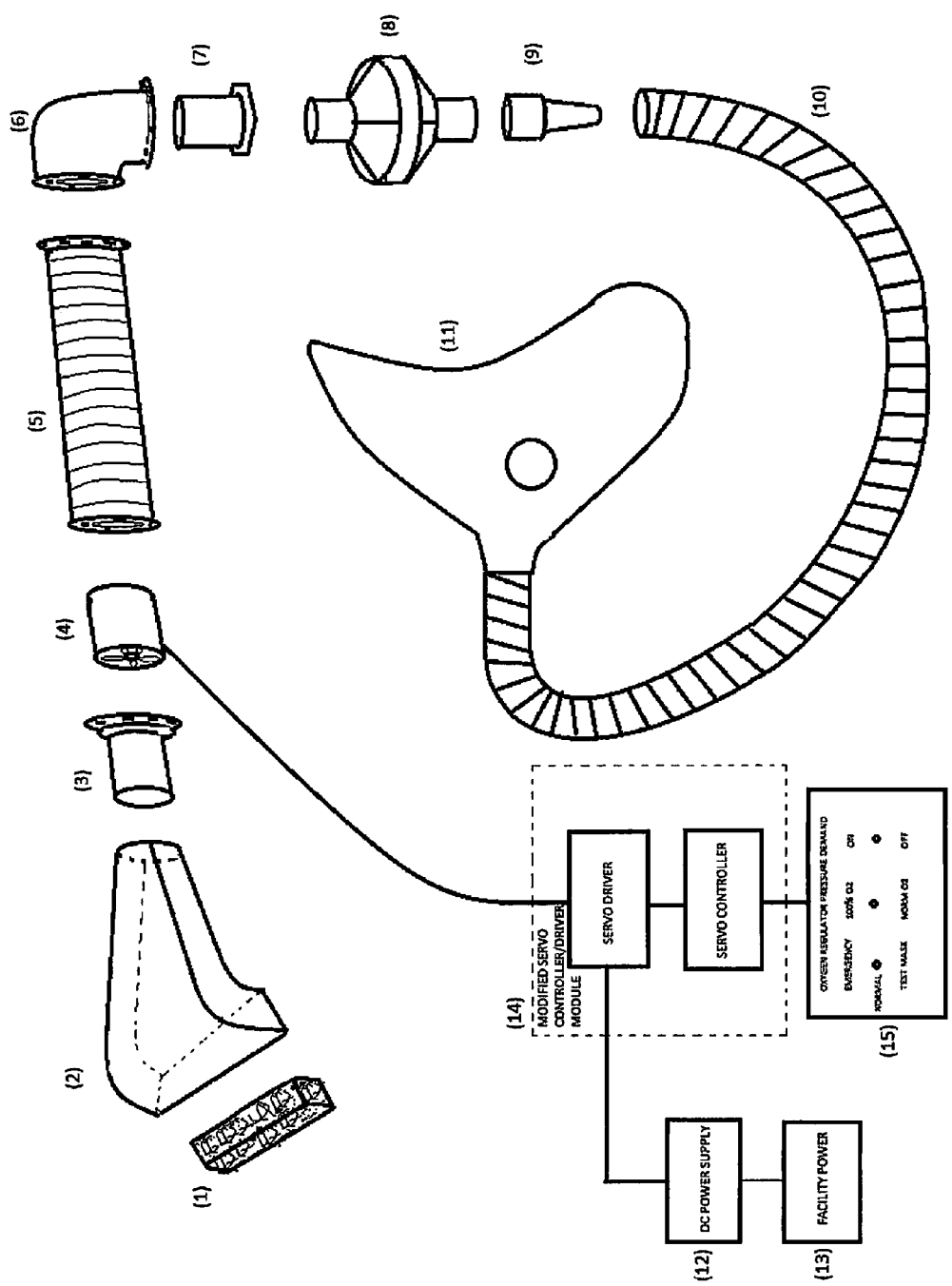
FIG. 1 is an illustration of a hypoxia recovery unit showing the assembly of its hardware components, and the electric connections to the power panel and the control component.

The inventive hypoxia recovery system is capable of preventing hypoxia in observer/instructors while providing hypoxia recovery to trainees in a normobaric mask off hypoxia training environment. FIG. 1 shows an embodiment of inventive hypoxia recovery system, which comprises a mock aircraft oxygen regulator, an air delivery system, and a control system.

The air delivery system further comprises an ambient air inlet (2), which may be fitted with a coarse filter material (1). This coarse filter prevents large debris, such as insect, small foreign objects and dusts, from entering the airway with the intake air. It may be made of any of the commercially available air filter materials. In the prototype system, as shown in FIG. 1, the ambient air intake (2) is a plastic funnel shaped chamber that is foam insulated to mitigate the noise generated by the rotation of the turbine fan motor (4). The air intake may also be made of other rigid and semi-rigid materials, such as metal, fiberglass, carbon fiber and alloys. The outlet of the ambient air intake (2) is then connected to a turbine fan motor (4). In a preferred embodiment the ducted turbine fan motor may be encapsulated in a modified, insulated, rigid PVC plastic AC duct fitting. The insulated PVC housing is used to reduce noise and provide for a means of sealing and securing the turbine fan motor. In the prototype, a small DC powered turbine fan motor (4) of approximately 40,000 rpm is used to generate the desired flow rates at a low positive pressure in order to supply adequate ambient air to users during different hypoxia training settings. A plastic circular quick disconnect fitting (3) was adapted to house the turban fan motor and connect it to air inlet. The air intake and the turbine fan motor are in fluid communication with a piece of flexible duct tubing. The turbine fan is adapted to pull ambient air from outside the normobaric chamber via the air intake (2) through a filter material (1), and expel the air down the flexible duct tubing, and supply it to the aviator's breathing mask wore by a user. The flexible duct tubing also serves as an air accumulator to provide a reserved amount of ambient air to the trainee during labored breathing as he/she recovers from altitude induced hypoxia. In the prototype system, the outlet of the turbine fan motor is connected via a quick connect coupling to a piece of approximately 3-feet 2 inch diameter wire reinforced, insulated, foil wrapped, flexible duct tubing (5). This flexible duct tubing is a spacepak sound attenuating tubing (Mestek, BM-6926), which comprises a porous inner tube reinforced by flexible wire, enclosed by a 1 inch thick fiber insulation, and sealed by the foil tape. The construction of this flexible duct tubing provides additional air storage of approximate 565 cubic inches as the said foil covered duct tubing expands, during turbine fan operation. This air storage supplies additional air to a trainee when the trainee's inspired air demand is greater during a hypoxia training scenario. This feature of the said foil covered insulated duct tubing is necessary as it prevents the trainee from further adverse effects caused by air starvation during his/her hypoxia recovery. Additional plumbing parts are used in the prototype system to route air into the normobaric chamber. The air is exhausted out of the turbine fan motor (4) and sent down the length of this duct tubing (5), which is mated to one end of a 90 degree radius quick connect elbow (6), who's opposite end has been modified to accept a ¾ inch PVC bulkhead fitting (7). This bulkhead fitting transitions through the ceiling panel of the mask off training room, and is coupled to a medical grade post filter (8). The medical grant post filter is used to capture any micron level debris and prevent it from entering the aviators breathing hose (10). The medical grade filter is modified with a barbed fitting (9) to connect it to inlet of an aviator's oxygen hose (10). The outlet of the aviators breathing hose (10) is then connected to an aviator's breathing mask (11). In a preferred embodiment, the aviator's mask has a one-way valve allows the exhalation of the expired air by the trainee to be released into the surrounding environment.

Figure 2:
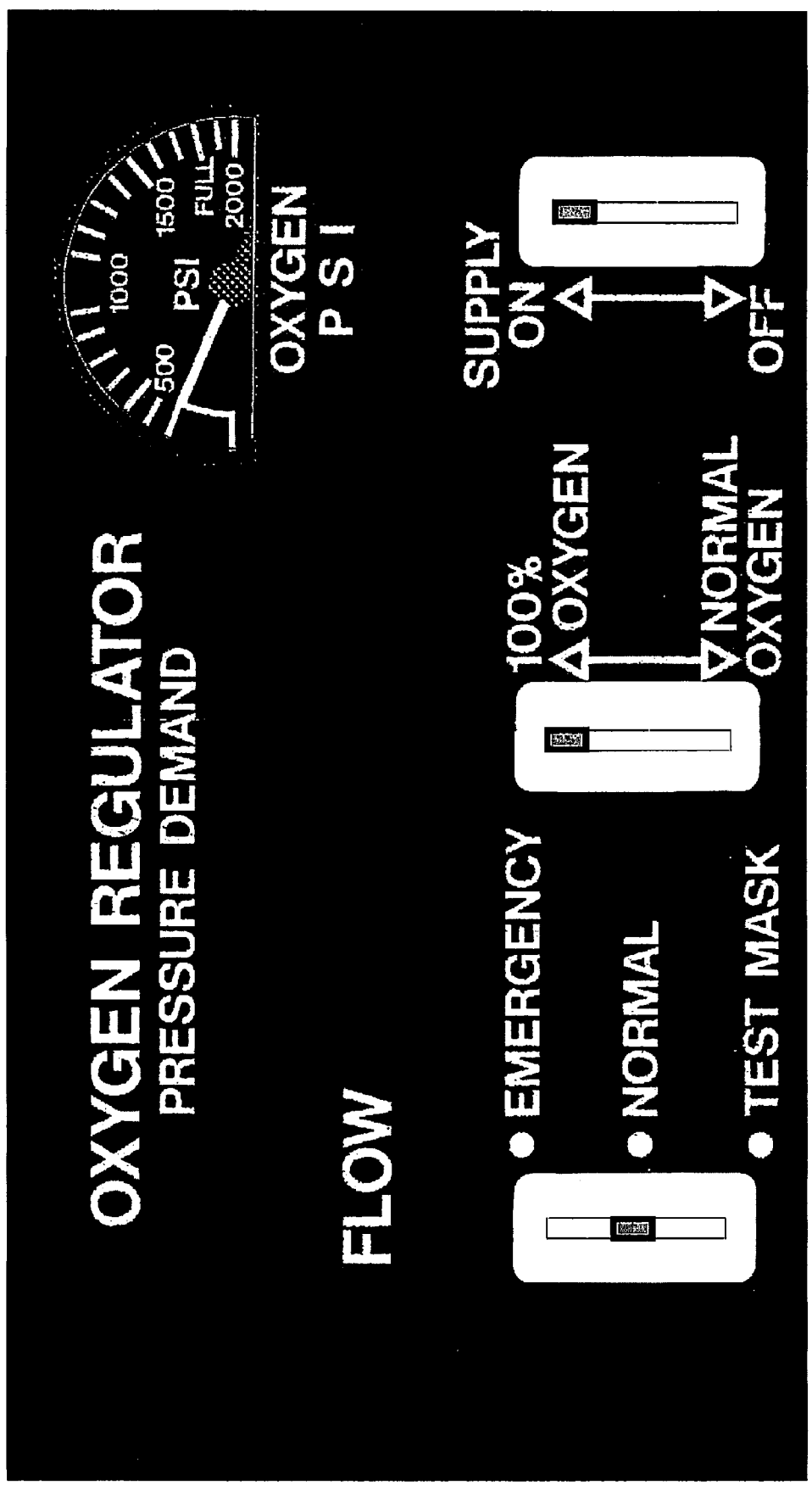
FIG. 2 is an illustration of control display of a mock MD-1 aircraft panel mounted oxygen regulator used in this invention.
Figure 3:
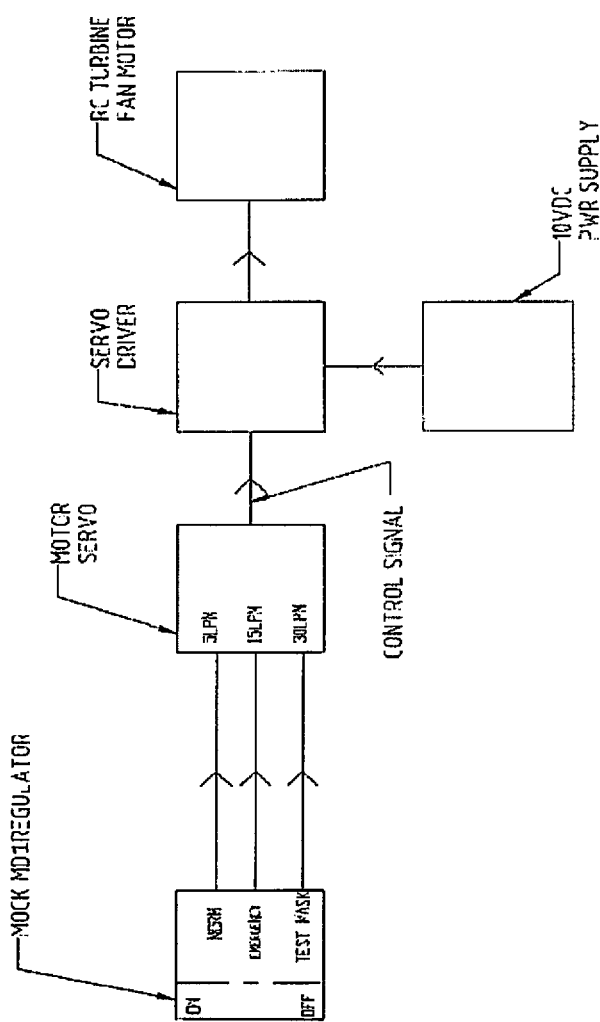
FIG. 3 is an illustration of a flow chart showing the control process.

The mock aircraft oxygen regulator is used to control airflow (i.e. oxygen supply) to the aviator's mask. The mock aircraft oxygen regulator (15) is operatively connected to a servo controller/driver electronic module (14), which has been modified for this invention's unique application. The servo controller/driver electronic control module (14), provides the proper voltage, current, and pulse width modulation, needed to control the speed of the turbine fan motor (4), as determined by the selected setting of the mock aircraft regulator (15). An embodiment of a mock aircraft oxygen regulator of this invention is a mock panel mount MD-1 aircraft regulator (15), whose display is shown in FIG. 2. The aircraft oxygen regulator (15) incorporates an On/Off switch, which is used to turn the turbine fan on or off, and a three position mode switch, which is used to change the speed of the turbine fan motor (4), and provide positive pressure air at three different flow rates, to the aviator's breathing mask (11).

Figure 4:
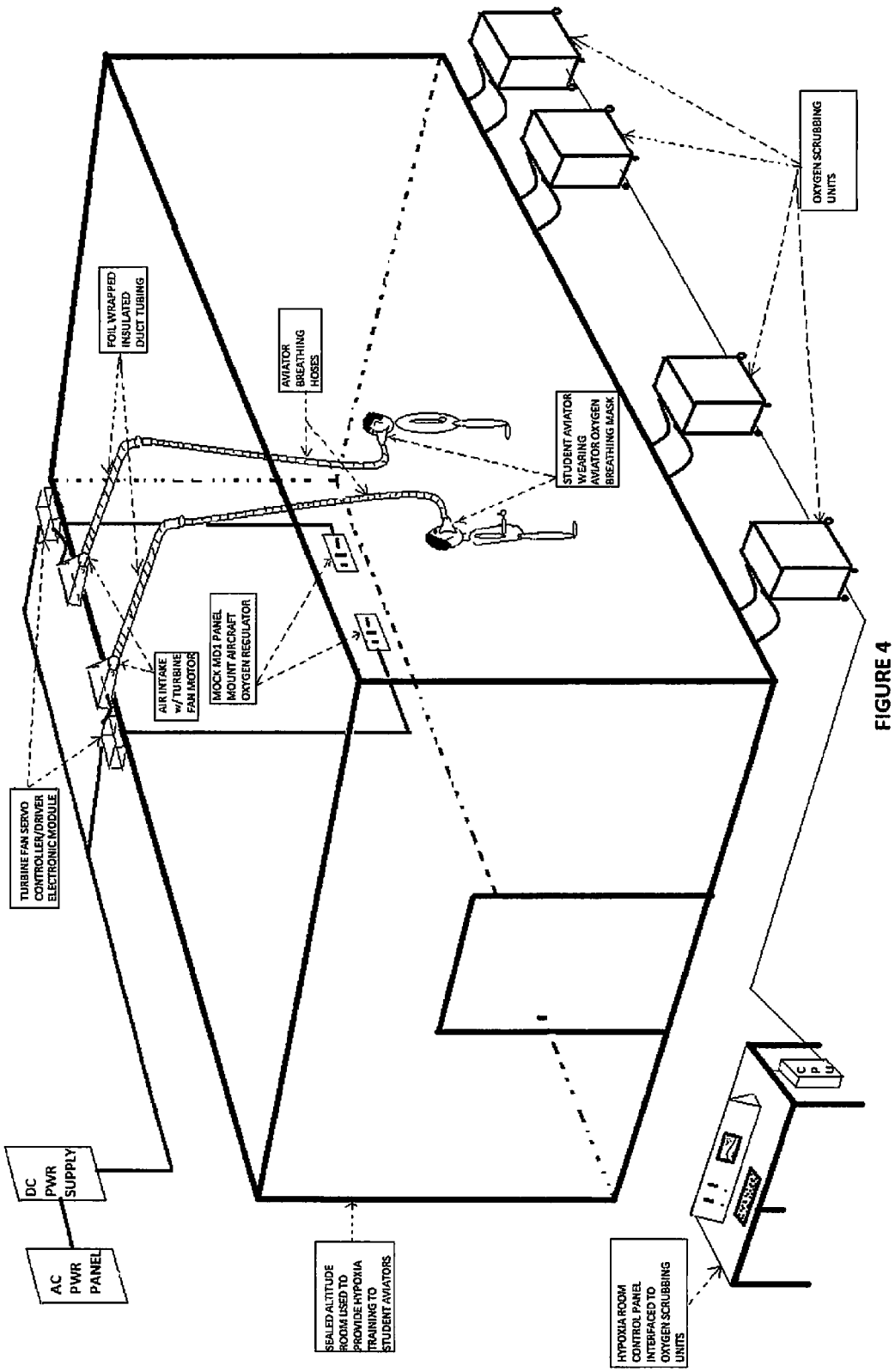
FIG. 4 is an illustration of the operation of the inventive hypoxia recovery unit during an aviation hypoxia training exercise.

As shown in FIG. 1, a ducted turban fan motor (4) is operatively connected to a direct current power source (12), using a solid state servo controller/driver electronic control module (14), which is controlled by the servo controller/driver electronic control module (14). The servo controller/driver is modified to cause the servo driver to operate the turbine fan motor at three distinct rotational speeds. The three fan speeds supply breathing air to the student aviator at an oxygen concentration of approximately 20.9% oxygen (which is the oxygen content of air at sea-level), to the aviator's breathing mask (11) at the relative flow rates of 5, 15 and 30 liters per minute (FIG. 4). Ambient air (sea level) is retrieved from outside the normobaric hypoxia training chamber. The speed settings for the turbine fan motor (4) correspond to the modes of operation of the mock oxygen regulator (15) which are: NORMAL, EMERGENCY and TEST MASK (FIG. 2). This design allows the system to look, operate and perform as an actual aircraft oxygen regulator. In an embodiment of the invention, the mock aircraft regulator models after an actual MD-1 regulator (FIG. 2) that is used in several the multi-crew aircraft. The mock oxygen regulator has controls and indicators which are located on the front panel of the regulator. The FLOW panel indicates the flow of oxygen through the regulator by a visible blinking action. The pressure gauge is found on the upper right of the panel and indicates inlet pressure to the regulator. The regulator (FIG. 2) has three control levers. A supply valve controller lever, located on the lower right corner, is used to control the supply of oxygen to the regulator. An emergency pressure control lever, located on the lower left of the panel, has three positions: EMERGENCY, NORMAL, and TEST MASK. On an actual MD-1 oxygen regulator, in the NORMAL OXYGEN position, the regulator delivers a mixture of air and oxygen with the air content decreasing until a cabin altitude of approximately 30,000 feet is reached. Above this altitude, 100-percent oxygen is delivered to the user upon inhalation. With the pressure control lever in the EMERGENCY position, the regulator delivers positive oxygen pressure at approximately 15 liters per minute flow rate, to the aviator's mask at altitudes. Positive pressured oxygen is not delivered in the NORMAL OXYGEN position. The positive pressured oxygen delivered during the EMERGENCY mode of operation, helps push oxygen into the alveoli of the lungs as altitude increases, and the NORMAL (demand) mode of operation is not sufficient to supply the needed oxygen to the aviator. The TEST MASK position is only used for checking the fit of the mask. Oxygen is delivered to the mask at flow rate of approximately 30 liters per minute, and the resultant pressure will be too high for an aviator to breath and thus used to check the fit (air seal) of a mask. The switch must be in the NORMAL position to assure normal system operation. With a real MD-1 regulator, the "NORMAL" mode of operation is an "on demand" regulator. The amount of inspired oxygen is determined by the demand of the test subject during respiration. In a preferred embodiment of this invention, it is necessary to simplify the NORMAL "on demand" mode of operation of a real MD-1 regulator, with respect to the NORMAL mode of operation during the use of the mock MD-1 regulator. As such, it was not necessary have the mock MD-1 regulator perform as a demand regulator in this mode of operation, but to deliver air to the student aviator/instructor's mask at a positive pressure of approximately 5 liters per minute flow rate. This feature simplifies the nature of this invention's design, yet provides a small amount of air flow to the aviator's mask, which in turn prevents air starvation, labored breathing and hyperventilating ($CO_2$) induced hypoxia, which occurs when they breathe on a static aviator mask (i.e. no air exchange occurs at the mask).

During a hypoxia training, when the aircrew/observers, transition into the hypoxia training chamber, they will immediately be subjected to a low oxygen environment. To prevent hypoxia from occurring prematurely, prior to the beginning of a training exercise, the aircrews/observer will be asked to wear their aviator's mask, and place their "mock" MD-1 panel mount aircraft regulator in the "NORMAL" mode of operation. During hypoxia training, they will be asked to take off the mask. With the normobaric chamber simulate cabin environment at different altitudes, the trainees will be ask to recognize their individual signs of hypoxia, and run hypoxia recovery practice drills using EMEMERGY setting. Trainees as well as observers/instructors who enters the normobaric chamber will be first asked to test for mask fit before each hypoxia training session using TEST MASK setting to ensure their safety. After the trainees have completed the hypoxia training exercise, they will be told to place their "mock" MD-1 regulator back in the "NORMAL" mode of operation as they await their departure from the altitude training chamber. Placing their "mock" MD-1 regulators in the "NORMAL" mode of operation, both prior to and after their training exercise, will give them a constant 5 LPM of constant air flow. The inside medical observers will wear his/her aviator's mask during their entire stay in the hypoxia training room, and have his/her "mock" MD-1 regulators always in the "NORMAL" mode of operation. This will provide them with a constant 5 LPM of air flow, so they can assist students during training, without succumbing to the effects of hypoxia.

FIG. 4 shows the operation of the inventive hypoxia recovery system in a normobaric chamber. A normobaric chamber to be used for mask off hypoxia training compatible with the inventive hypoxia recovery system is a sealed environment made of any type of non-rigid material. The sea level ambient air within the sealed environment is pumped out using oxygen scrubbing device. Air is then pumped back into the room, but at a much lower oxygen concentration to simulate any given altitude, of which provide the trainee with a hypoxia inducing environment. The interior of the room is user configured to house flight crew simulator stations that provide realistic in-flight tasking for the students. Each station is pre-programmed with routine aviation and emergency tasks designed for the aircrew manning that station. The trainee, during hypoxia recognition and recovery training, are asked to carry out required tasks that they would normally engage in during normal flight, such as navigation, flying, or operating weapons systems, as they slowly and unknowingly become hypoxic. This invention provides standalone hypoxia recovery systems for each aircrew/observer station, to deliver positive pressure breathing air to a student/instructor during hypoxia training.

EXAMPLE 1

Testing and Evaluation of a Real MD-1 Aviator Oxygen Regulator, as Used in an Aircraft, and in Hypobaric Chambers During the design and testing of this hypoxia recovery system invention, flow rates within an aviator mask were measured at the three mode switch settings, of 10 MD-1 real aircraft oxygen regulators. This was done in order to establish the mean average, and basis for the flow rates which would be required for this invention. Breathing loop pressure was measured, and was determined to be no more than 10 inches of water, and the volumetric size of the needed reserve was also determined.

EXAMPLE 2

Testing and Evaluation of the Positive Pressure Turbine Fan, Hypoxia Recovery Device Invention During the design and prototype testing of this invention, 5 subjects were fitted with an aviator's mask, and were subjectively yet independently used measured inside a CAT altitude chamber with typical student hose configuration, using panel mounted mock MD-1 aviation regulator. 100% Oxygen flow rates for MD-1 regulator was determined at 5, 15, and 30 liter per minute (LPM), for the three operational modes: NORMAL, EMERGENCY, and TEST MASK.

An evaluation of the invention, in order to determine the proper flow rates, and other specifications, was repeated 3 times with 5 subjects, as they were fitted with an aviator's masks and performed hypoxia recovery training evolutions using the Positive Pressure Turbine Fan Hypoxia Recovery Device invention and mock MD-1 regulators. After collecting and averaging the data from the testing in Example 1, and the evaluation in Example 2, it was determined that the preferred flow rates for the three modes of operation for the mock MD-1 regulator and Positive Pressure Hypoxia Recovery Device; NORMAL, EMERGENCY, and TEST MASK, be 5 LPM, 15 LPM and 30 LPM, respectively.

The invention claimed is:

1. A hypoxia recovery system for normobaric chamber, comprising
   a) an ambient air inlet;
   b) an aviator's oxygen mask equipped with an aviator hose;
   c) a flexible duct tubing connected to said aviator hose;
   d) a turbine fan motor is in fluid communication to said ambient air inlet and said flexible duct tubing, wherein said fan motor is adapted to pull in ambient air from said air inlet and expel it down said flexible duct tubing and supply it to a subject through said aviator's oxygen mask;
   e) a servo controller/driver operatively connected to said turbine fan motor and an oxygen regulator, where said controller/driver is controlled by oxygen regulator and capable of changing the speed of the turbine fan motor; and
   f) a power supply operatively connected and supplies power to the turbine fan motor, the servo controller/driver and the oxygen regulator.

2. The hypoxia recovery system of claim 1, wherein said ambient air has oxygen content equivalent to air at sea level atmosphere pressure.

3. The hypoxia recovery system of claim 1, wherein said aviator's mask has a one-way valve allowing exhaled expired air from said subject to be released into the surrounding environment.

4. The hypoxia recovery system of claim 1, wherein said servo controller/driver is programed to operate the turbine fan motor at three speeds which supplying air to said subject at flow rate of 5 liters per minute, 15 liters per minute and 30 liters per minute.

5. The hypoxia recovery system of claim 4, wherein said turbine fan motor can be controlled through said oxygen regulator.

6. The hypoxia recovery system of claim 1, wherein said power supply is an AC or DC source.

7. The hypoxia recovery system of claim 1, wherein said flexible air duct tubing is a wire reinforced, foil wrapped, insulated tube.

8. The hypoxia recovery system of claim 1, wherein said flexible air duct provides additional air storage.

9. The hypoxia recovery system of claim 1, wherein said power supply is an AC or DC source.

10. The hypoxia recovery system of claim 1, wherein said flexible duct tubing is a foil covered insulted AC duct tubing.

* * * * *